US006365338B1

(12) United States Patent
Bull et al.

(10) Patent No.: US 6,365,338 B1
(45) Date of Patent: Apr. 2, 2002

(54) ORGAN PRESERVATIVE SOLUTION CONTAINING TREHALOSE, ANTI-OXIDANT, CATIONS AND AN ENERGY SOURCE

(76) Inventors: David A. Bull, 1298 Chandler Dr., Salt Lake City, UT (US) 84103; Bruce C. Reid, 471 N. 1100 East, Bountiful, UT (US) 84010; James C. Stringham, 1124 Augusta Way; Shreekanth V. Karwande, 1028 Crestview Cir., both of Salt Lake City, UT (US) 84108

( * ) Notice: Subject to any disclaimer, the term of this patent is extended or adjusted under 35 U.S.C. 154(b) by 0 days.

(21) Appl. No.: 09/299,894

(22) Filed: Apr. 27, 1999

(51) Int. Cl.$^7$ ................................................. A01N 1/02
(52) U.S. Cl. ........................................................ 435/1.1
(58) Field of Search ........................... 435/1.1, 1.2, 1.3

(56) References Cited

U.S. PATENT DOCUMENTS

| | | |
|---|---|---|
| 4,798,824 A | 1/1989 | Belzer et al. |
| 4,873,230 A | 10/1989 | Belzer et al. |
| 4,879,283 A | 11/1989 | Belzer et al. |
| 4,938,961 A | 7/1990 | Collins et al. |
| 5,328,821 A | 7/1994 | Fisher et al. |
| 5,370,989 A | 12/1994 | Stern et al. |
| 5,405,742 A | 4/1995 | Taylor et al. |
| 5,407,793 A | 4/1995 | Del Nido et al. |
| 5,432,053 A | 7/1995 | Berdyaev et al. |
| 5,552,267 A | 9/1996 | Stern et al. |
| 5,565,317 A | 10/1996 | Dohi et al. |

OTHER PUBLICATIONS

Grant & Hackh's Chemical Dictionary, Fifth Ed., 1987, p. 463, polysaccharides.*
Amrani et al., "The effect of L-arginine on Myocardial Recovery after Cardioplegic Arrest.", Circulation 96 (9 Supp.) II–274–9 (1996).*
Stowe et al., "Effects of L-arginine and N-omega-nitro-L-arginine methyl ester on cardiac perfusion and function after 1-day cold preservation of isolated hearts", Circulation 95 (6): 1623–34 (1997).*
Yang et al., "The roles of reactive oxygen species and endogenous opiod peptides in ischemiz-induced arrhyhmia of isolated rat hearts", Free RAdical Biology and Medicine 18 (3) : 593–8 (1995).*
Belzer, Folkert O. and James H. Southard, "Principles of Solid-Organ Preservation by Cold Storage," *Transplantation*, Apr. 1988, 45(4):673–6.
Collins, G. M. et al., "Kidney Preservation for Transportation," *The Lancet*, Dec. 6, 1969, 2:1219–22.
Demmy, Todd L. et al., "Organ Preservation Solutions in Heart Transplantation—Patterns of Usage and Related Survival," *Transplantation*, Jan. 27, 1997, 63:262–9.
Fisher, Robyn et al., "Cryopreservation of Pig and Human Liver Slices," *Cryobiology*, 1991, 28:131–42.
Fisher, Robyn et al., "Cold-and Cryopreservation of Human Liver and Kidney Slices," *Cryobiology*, 1993, 30:250–61.
Fisher, Robyn et al., "Cold-and Cryopreservation of Dog Liver and Kidney Slices," *Cryobiology*, 1996, 33:163–71.
Gandolfi, A. Jay et al, "Use of Tissue Slices in Chemical Mixture Toxicology and Interspecies Investigations," *Toxicology*, 1995, 105:285–90.
Jeevanandam, Valluwan et al., "Cardiac Transplantation After Prolonged Graft Preservation with The University of Wisconsin Solution," *The Journal of Thoracic and Cardiovascular Surgery*, Aug. 1992, 104(2): 224–8.
Keshavjee, S. H. et al., "A Method for Safe Twelve-Hour Pulmonary Preservation," *The Journal of Thoracic and Cardiovascular Surgery*, Oct. 1989, 98(4):529–34.
Oz, Mehmet C. et al., "Novel Preservation Solution Permits 24-Hour Preservation in Rat and Baboon Cardiac Transplant Models," *Circulation*, Nov. 1993, 88:II–291–7.
Parrish, Alan R. et al., "Mini Review Precision-Cut Tissue Slices: Applications in Pharmacology and Toxicology," *Life Sciences*, 1995, 57:1887–901.
Shiraishi, Yuji et al, "L-Arginine Administration During Reprefusion Improves Pulmonary Function," *Annual Thoracic Surgery*, 1996, 62:1580–7.
Wada, Hiromi et al., "ET–Kyoto Solution for 48–Hour Canine Lung Preservation," *Annuals of Thoracic Surgery*, 1996, 61:963–8.

* cited by examiner

*Primary Examiner*—Sandra E. Saucier
(74) *Attorney, Agent, or Firm*—Mandel & Adriano

(57) ABSTRACT

The present invention is organ and tissue preservation solutions that provide improved viability of an organ such as a heart or lung, or portion of the organ, for storage and transplantation. In particular, a solution contains trehalose, magnesium sulfate, calcium chloride, heparin, dextran, nitroglycerin, adenosine, L-arginine, allopurinol, reduced glutathione, db-cylic AMP and potassium phosphate.

25 Claims, 4 Drawing Sheets

ORGAN PRESERVATIVE SOLUTION CONTAINING TREHALOSE, ANTI-OXIDANT, CATIONS AND AN ENERGY SOURCE

FIELD OF THE INVENTION

The present invention relates to a novel solution for preserving and maintaining organs and portions thereof, in particular heart and myocardial tissue and lung and lung tissue.

BACKGROUND OF THE INVENTION

Preservation of the viability of donor organs continues to be an important goal in transplantation. Typically the organ to be transplanted must be stored and shipped to the prospective recipient. The ability to prolong the cellular viability of the organ during storage and transportation is very important to the success of the transplant operation. Preservative solutions play an important role in the longevity of the organ. Prior known solutions for organ preservation include those described by Berdyaev et al., U.S. Pat. No. 5,432,053; Belzer et al., U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. No. 5,370,989 and 5,552,267.

Currently there is no consensus among practitioners regarding an optimal solution for heart preservation. Solutions include those classified as intracellular ([Na++]<70 mEq/L) or extracellular ([Na++]≧70 mEq/L). A recent survey showed that there were at least 167 organ preservation solutions available for heart transplantation, and that there was significant variation in solution usage observed among major U.S. regions of transplantation activity. (Demmy et al., Organ preservation solutions in heart transplantation—patterns of usage and related survival. *Transplantation* 63(2): 262–269 (1997)). Presently known solutions for cardiac preservation include those described by Oz et al., Novel Preservation Solution Permits 24-Hour Preservation in Rat and Baboon Cardiac Transplant Models, *Circulation* 88(2)L291–297 (1993) at Columbia University in New York, and Belzer and Southard in *Transplantation* 45:673–676 (1988), at the University of Wisconsin. Other solutions for heart preservation and cardioplegia include those disclosed in U.S. Pat. No. 5,407,793 by Del Nido at al. (Univ. Of Pittsburgh); and U.S. Pat. No. 4,938,961 by Collins et al.).

The development of myocardial preservation solutions typically requires the use of whole organ models to assess the performance of such solutions. These methods are animal and labor intensive. In addition such methods rely on physiologic rather than biochemical endpoints, making accurate comparison of the relative efficacy of individual solution components difficult. Another problem inherent in the whole organ test model is that individual responses can not be removed as a variable when organs must be harvested from many different donors to be tested.

The use of tissue slices have advantages over both in vivo whole organ models and in vitro cellular models to study organ function. Advantages over whole organ models include a reduction in the number of animals used, a decrease in experimental variation, more rapid production of experimental results and elimination of humoral and neuronal systemic influences. (Fisher et al., *Cryobiology* 33:163 (1996)). Preservation and homogenization of tissue in a measured, standardized fashion is much simpler using slices rather than whole organs, facilitating the measurement of quantifiable biochemical endpoints. As a result, comparative experiments that typically would take several weeks using whole organs can be done in two days using the slice model.

Compared to cell culture or cell suspension models, tissue slices maintain the multicellular composition of intact tissue, preserving the intercellular connections used in maintaining contact inhibition, signal transmission and hormonal and ion transport (Fisher et al., *Cryobiology* 33:163 (1996)). These intercellular connections are typically lost with the protease digestion necessary to isolate single cell types used with in vitro models (Fisher et al., *supra*). In addition, with optimization of the slice thickness, efficient gas and nutrient exchange can be maintained with diffusion into the tissue of entering nutrients and oxygen and egress of cellular byproducts. (Fisher et al., *supra*). As a result of these physiologic advantages and the efficiencies of the tissue slice model, individual solution components can be readily studied for their contribution to one or more measures of myocardial preservation.

The use of organ slices for in vitro toxicological and metabolic studies of potential drugs and environmental contaminants has been described for various organs including the liver. (Fisher et al., *Cryobiology* 28: 131–142 (1991); Fisher et al., *Cryobiology* 30:250–261 (1993); Fisher et al., U.S. Pat. No. 5,328,821 and Gandolfi et al., *Toxicology* 105:2–3, 2850290 (1995). Heart tissue slices have been used in pharmacology and toxicology tests to evaluate cold and cryopreservation solutions (Parrish et al., *Life Sci.* 57:21 (1887–901 (1995)).

Assessment of cellular viability is a requirement for determining effectiveness of tissue preservation with cold storage. Preservation of myocardial cellular viability can be assessed by measurement of ATP levels and capacity for protein synthesis. ATP levels are critical in the stored heart for energy production during and following reperfusion. Capacity for protein synthesis is a general indicator of cellular viability because it requires the integration of several complex biochemical pathways.

There remains a need for improved solutions to preserve viability and maintain function of donor organs for transplantation and research.

SUMMARY OF THE INVENTION

Accordingly, the invention comprises novel solutions for preserving and maintaining the viability of solid tissue such as organs and portions thereof, particularly heart and lung tissue. The solutions contain a sufficient amount of a cryopreservative agent, anti-oxidant and an energy source to support intracellular function and maintain cellular viability. The cryopreservative agent can be a chain of simple sugars including disaccharides, trisaccharides, or a chain of four or more saccharides; one example is trehalose. The anti-oxidant can be glutathione and/or allopurinol, and the energy source is cyclic AMP, cyclic GMP or adenosine. The solution can further contain cations such as calcium, potassium and magnesium, an anticoagulant such as heparin, a polysaccharide such as dextran, nitroglycerin and at least one amino acid, for example, L-arginine and is at a pH of from 7.0 to 8.0.

An embodiment of the solution of the invention for preservation and maintenance of the viability of heart tissue includes the following components:

from 0.01 g/L to 10 g/L of cations;

from 3 g/L to 100 g/L of a polysaccharide cryopreservative agent;

from 100 to 30,000 units/L of an anticoagulant;

from 25 g/L to 40 g/L of a polysaccharide;
from 10 mg/L to 1000 mg/L of nitroglycerin;
from 0.10 g/L to 10 g/L of an amino acid;
from 0.01 g/L to 10 g/L of an anti-oxidant; and
from 0.01 g/L to 10 g/L of an energy source, at a pH of approximately 7.4.

A preferred embodiment of the solution of the invention for preservation and maintenance of the viability of heart tissue includes the following components:

2.72 g/L potassium phosphate (20 mmol/L)
1.93 g/L magnesium sulfate (15 mmol/L)
0.11 g/L calcium chloride (1 mmol/L)
30.0 g/L trehalose
10,000 units/L heparin
30.0 g/L dextran
100 mg/L nitroglycerin
1.34 g/L adenosine (5 mmol/L)
1.74 g/L L-arginine (10 mmol/L)
0.14 g/L allopurinol (1 mmol/L)
0.92 g/L glutathione (reduced, 3 mmol/L) and
0.98 g/L db-cyclic AMP (2 mmol/L) at a pH of 7.4.

The invention includes a method of preserving and/or maintaining an organ or tissue by contacting it with a solution of the invention, and a method of transplantation by grafting an organ or tissue and perfusing it with the solution of the invention.

Another embodiment of the solution of the invention for preservation and protection of lung tissue includes the following components:

from 0.01 g/L to 10 g/L cations;
from 3 g/L to 100 g/L of a polysaccharide cryopreservative agent;
from 100 units/L to 30,000 units/L of an anticoagulant;
from 25 g/L to 40 g/L of polysaccharide;
from 10 mg/L to 1000 mg/L of nitroglycerin;
from 0.01 g/L to 10 g/L of an antioxidant; and
from 0.01 g/L to 10 g/L of an energy source, at a pH of from 7 to 8.

In a preferred embodiment, the solution of the invention for lung tissue contains magnesium, calcium and potassium ions, the polysaccharide cryopreservative trehalose, the anticoagulant heparin, the polysaccharide dextran, the amino acid arginine, the antioxidant glutathione and/or allopurinol, and cyclic GMP, cyclic AMP or adenosine as the energy source.

In a particularly preferred embodiment of the solution for lung, the solution contains the following components:

2.72 g/L potassium phosphate (20 mmol/L)
1.93 g/L magnesium sulfate (15 mmol/L)
0.11 g/L calcium chloride (1 mmol/L)
30.0 g/L trehalose
10,000 units/L heparin
30.0 g/L dextran
100 mg/L nitroglycerin
1.34 g/L adenosine (5 mmol/L)
0.14 g/L allopurinol (1 mmol/L)
0.92 g/L glutathione (reduced, 3 mmol/L)
89.2 mg/L 8-Bromo-c-GMP (200 mmol/L) and
16.0 mg/L Dexamethasone at a pH of 7.4.

DETAILED DESCRIPTION OF THE INVENTION

Figure 1:
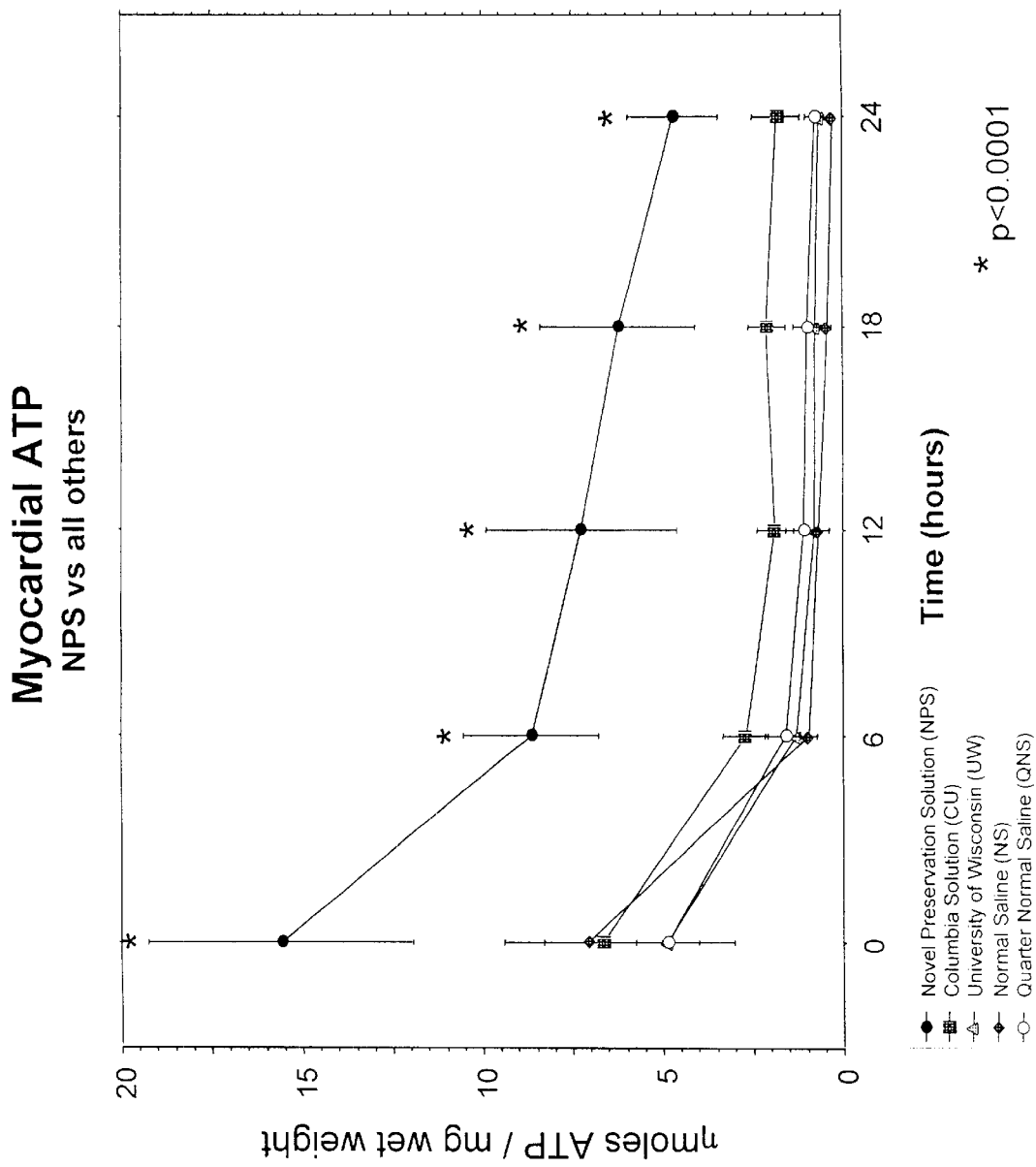
FIG. 1 is graph of the ATP content of myocardial tissue, bathed in 5 different preservation solutions, described in the example, infra.

The invention provides solutions for tissue preservation and protection of organs and portions of the organs such as heart and lung. In one embodiment of the invention, a heart solution includes a cryopreservative agent, such as a chain of simple sugars including disaccharides, trisaccharides, or a chain of four or more saccharides, for example trehalose, an anti-oxidant such as allopurinol, and an energy source such as cyclic AMP, cyclic GMP or adenosine, in an amount sufficient to support intracellular function and maintain cellular viability. The solution also contains sources of cations, for example, potassium, calcium and magnesium ions, in the form of potassium phosphate monobasic, calcium chloride, and magnesium sulfate, a polysaccharide such as dextran, an amino acid such as Larginine, at least one anti-oxidant such as glutathione (reduced) and/or allopurinol, nitroglycerin, an energy source such as dibutyryl cyclic AMP, cyclic GMP or adenosine, and an anticoagulant, preferably heparin. The solution is adjusted to a pH of between 7 and 8 with a suitable buffer such as potassium hydroxide or sodium hydroxide.

In general, the following ranges of ingredients may be used:

from 0.01 g/L to 10 g/L of cations;
from 3 g/L to 100 g/L of a polysaccharide cryopreservative agent such as trehalose
from 100 to 30,000 units/L of an anticoagulant such as heparin;
from 25 g/L to 40 g/L of polysaccharide such as dextran,
from 10 mg/L to 1000 mg/L of nitroglycerin
from 0.10 g/L to 10 g/L of amino acids such as L-arginine
from 0.01 g/L to 10 g/L of an anti-oxidant such as glutathione (reduced) and/or
from 0.01 g/L to 10 g/L of allopurinol; and
from 0.01 g/L to 10 g/L of an energy source such as cyclic AMP, cyclic GMP or adenosine A preferred embodiment of the heart solution of the invention is as follows:

2.72 g/L potassium phosphate (20 mmol/L)
1.93 g/L magnesium sulfate (15 mmol/L)
0.11 g/L calcium chloride (1 mmol/L)
30.0 g/L trehalose
10,000 units/L heparin
30.0 g/L dextran
100 mg/L nitroglycerin
1.34 g/L adenosine (5 mmol/L)
1.74 g/L L-arginine (10 mmol/L)
0.14 g/L allopurinol (1 mmol/L)
0.92 g/L glutathione (reduced, 3 mmol/L); and
0.98 g/L dbcyclic AMP (2 mmol/L) at a pH of 7.4.

The lung preservation solution of the invention includes a polysaccharide such as dextran in an amount sufficient to support intracellular function and maintain cellular viability, and a cryopreservative polysaccharide such as trehalose. The solution also contains sources of potassium, calcium and magnesium ions such as potassium phosphate monobasic, calcium chloride, and magnesium sulfate, an amino acid such as adenosine, at least one anti-oxidant such as glutathione (reduced) and/or allopurinol, nitroglycerin, an energy source such as 8-Bromo-c-GWP or cyclic AMP, an anticoagulant, preferably heparin and a cell membrane stabilizer such as dexamethasone to preserve cellular integrity. The solution is adjusted to a pH of between 7 and 8 with a suitable buffer such as potassium hydroxide or sodium hydroxide.

In general, the following ranges of ingredients may be used:

from 0.01 g/L to 10 g/L of K, Mg and Ca ions;

from 3 g/L to 100 g/L of a polysaccharide cryopreservative agent such as trehalose from 100 units/L to 30,000 units/L of an anticoagulant such as heparin;

from 25 g/L to 40 g/L of polysaccharide such as dextran, from 10 mg/L to 1000 mg/L of nitroglycerin from 0.01 g/L to 10 g/L of an anti-oxidant such as glutathione (reduced) and/or from 0.01 g/L to 10 g/L of allopurinol; and from 0.01 g/L to 10 g/L of an energy source such as 8-Bromocyclic-GMP, cyclic AMP or adenosine A preferred embodiment of the lung solution of the invention is as follows:

2.72 g/L potassium phosphate (20 mmol/L)

1.93 g/L magnesium sulfate (15 mmol/L)

0.11 g/L calcium chloride (1 mmol/L)

30.0 g/L trehalose 10,000 units/L heparin 30.0 g/L dextran 100 mg/L nitroglycerin at 5 mg/ml (0.1 mg/ml)

1.34 g/L adenosine (5 mmol/L)

0.14 g/L allopurinol (1 mmol/L)

0.92 g/L glutathione (reduced, 3 mmol/L)

89.2 mg/L 8-Bromo-c-GMP (200 mmol/L); and 16.0 mg/L Dexamethasone at a pH of 7.4.

USE OF THE INVENTION

The preservative solutions of the invention can be used to preserve and or protect organ tissue, or whole organs, when said organs or tissue are brought into contact with the solution. A specific embodiment of the invention is for the preservation of a human heart, or human myocardial tissue. Another embodiment of the invention is for the preservation of a human lung or human lung tissue. The invention contemplates the use of the solutions to preserve mammalian tissue, organs or portion thereof. In addition, the solutions can be used to facilitate transplantation of organs, e.g. by perfusion of the organ or tissue during the transplantation procedure. The solution can also be used as a cardioplegia solution in cardiac surgery. Preferably, the organ or portion thereof, is maintained in the appropriate solution at all times.

The solutions of the invention can be used to maintain viability of the organ or tissue during storage, transplantation or other surgery. The invention includes a method of storing tissue or organs comprising contacting said tissue, organ or part thereof, with the solution of the invention, such that the in vivo and/or in vitro viability is prolonged. The solutions permit maintenance of viability of heart or lung tissue for up to 24 hours. Use of the solutions of the invention results in improved organ viability as determined by ATP production and protein synthesis in vitro and in vivo as compared to other known solutions.

The solutions of the invention are tested to assess their performance to predict whole organ viability. The solutions of the invention are tested using tissue slices as described in the Examples infra. In these examples, a complete biochemical analysis was performed over 24 hours using only 2½ animal hearts (with approximately 20 slices/heart) as compared to the several week period required for comparative studies using whole hearts. These examples demonstrate that tissue slices can be used to compare preservation of organ biochemical function during cold storage in different preservation solutions for lung and the heart. The test system uses slices of myocardial tissue cut to approximately the optimal thickness for molecular transport, i.e. the thickness that permits the optimal amount of oxygen to diffuse through the tissues to maintain ATP production. The tissue slices are exposed to the preservation solutions of the invention for a time sufficient to determine the performance of the solution and/or its components with respect to maintaining viability of the tissue slices. Preferred tissue slice thickness ranges from 100 to 400 microns, and particularly 200 microns. Viability may be determined by measuring, for example, ATP production and protein synthesis, by the tissue slice in vitro. Performance of the preservation solutions of the invention on whole organs is also evaluated in animals as described in the example, infra.

The following examples are presented to demonstrate the methods and solutions of the present invention and to assist one of ordinary skill in making and using the same. The examples are not intended in any way to otherwise limit the scope of the disclosure or the protection granted by Letters Patent granted hereon.

EXAMPLE 1

Sprague-Dawley rats weighing 200 to 250 grams were anesthetized with halothane. Using strict sterile technique, a median sternotomy incision and cardiectomy of the whole rat heart was rapidly performed. The whole rat hearts were then placed in one of five cardiac preservation solutions: 1) solution 1("CU") (refer to Table 1); 2) solution 2 ("UW") (refer to Table 2); 3) normal saline ("NS"); 4) $D_5$ 0.2% normal saline with 20 Meq/l KCl ("QNS"), or 5) the solution of this invention ("NPS") (Table 3). Rat hearts were precision cut into 200 μm diameter slices using a mechanical tissue slicer (Vitron, Tucson, Ariz.) in each of the five (5) solutions (room temperature) and preserved at 4° C. for 6, 12, 18 or 24 hours in each solution. Six slices were stored at each time point for each solution in 100-ml flasks containing 50 ml of preservation solution. The flasks were gently shaken on an orbital shaker.

TABLE 1

| (CU solution) | |
|---|---|
| 50 g/L | dextran |
| 95 mmol/L | potassium gluconate |
| 25 mmol/L | potassium phosphate monobasic |
| 5 mmol/L | magnesium sulfate |
| 67 mmol/L | glucose |
| 5 mmol/L | adenosine |
| 50 micromol/L | butylated hydroxyanisole |
| 50 micromol/L | butylated hydroxytoluene |

TABLE 1-continued (CU solution)

| | |
|---|---|
| 0.05 mmol/L | N-Acetyl cysteine |
| 10 units/ml | heparin |
| 10 micromol/L | verapamil |
| 0.1 mg/ml | nitroglycerine and |
| 2 mmol/L | dibutyryl cyclic AMP |
| pH to 7.6 with potassium hydroxide | |

TABLE 2

(UW solution)

| | |
|---|---|
| 50 g/L | hydroxyethyl starch |
| 100 mmol/L | lactobionic acid |
| 25 mmol/L | potassium phosphate |
| 5 mmol/L | magnesium sulfate |
| 30 mmol/L | raffinose |
| 5 mmol/L | adenosine |
| 3 mmol/L | glutathione reduced |
| 16 mg/L | dexamethasone |
| 100 units/L | insulin |
| 1 mmol/L | allopurinol and |
| 160 mg/L to 32 mg/L | TMP-SMZ |
| pH to 7.4 using 25 mmol NaOH:KOH | |

The following ingredients and amounts were used to prepare the heart solution of the invention:

TABLE 3

(NPS solution)

| | |
|---|---|
| 2.72 g/L | potassium phosphate (20 mmol/L) |
| 1.93 g/L | magnesium sulfate (15 mmol/L) |
| 0.11 g/L | calcium chloride (1 mmol/L) |
| 30.0 g/L | trehalose |
| 10,000 units/L | heparin |
| 30.0 g/L | dextran |
| 100 mg/L | nitroglycerin |
| 1.34 g/L | adenosine (5 mmol/L) |
| 1.74 g/L | L-arginine (10 mmol/L) |
| 0.14 g/L | allopurinol (1 mmol/L) |
| 0.92 g/L | glutathione (reduced, 3 mmol/L) and |
| 0.98 g/L | db-cyclic AMP (2 mmol/L) |

The ingredients were added at room temperature stirring constantly. After adding the allopurinol, the solution was brought up to a volume of 980 ml using distilled water. 0.92 g/l of glutathione (reduced from, 3 mmol/l) was dissolved in 20 ml of distilled water and the pH adjusted to approximately 7.4 using potassium hydroxide (KOH). KOH was also used to bring the main solution up to a pH Of 7.4. After both solutions were at a pH of 7.4 the glutathione solution was added to the main solution. Then 0.98 g/l of db-cyclic AMP (2 mmol/L) was added and the final pH was adjusted to 7.4.

Myocardial biochemical function was assessed by ATP content and capacity for protein synthesis immediately following slicing (0 hours) and at 6, 12, 18 and 24 hours of preservation using each solution. ATP content was measured using a luciferin-luciferase bioluminescent assay. Following weighing the tissue slice was placed in 1 ml of 10% TCA, homogenized and then snap frozen in liquid nitrogen and stored at −80° C., When the collected specimens were ready for assay, the samples were thawed and then centrifuged (4200 rpm for 12 min). Ten ml of the supernatant was taken and diluted with 2 ml of BEPES buffer. Plastic tubes were used to minimize binding of the ATP. Two hundred ml of each sample was then pipetted into luminometer cuvettes (Sarstedt, 3584 Arden Road, Hayward, Calif.). The luciferin-luciferase solution was prepared to a volume of 15 ml using 30 ml of luciferase (Amgen Biologicals, Thousand Oaks, Calif.), 750 ml of luciferin (Sgma, St. Louis, Mo.), 7.5 ml of stabilizing buffer, and 6.75 ml of HEPES buffer. As a reference, an ATP standard was run for each set of ATP assays using an ATP stock solution at 10 mg/ml (Turner Instruments, Mountain View, Calif.) diluted appropriately with HEPES buffer to create 5 distinct solutions at 1, 10, 50, 100 and 200 ng/ml. ATP levels were then measured following addition of the luciferin-luciferase to each luminometer curvette using a luminometer referenced to the ATP standard.

The results are expressed as nanomoles of ATP/mg of wet weight of tissue. (FIG. 1). The data was analyzed using analysis of variance and are presented as the mean ± standard deviation. On average, twenty slices were obtained per whole rat heart. Time to completion of ATP levels for the 24-hour time frame of the study for each solution was 2 days. Mean values and standard variations demonstrated consistent variability.

As shown in FIG. 1, the ATP content for the slices, at each of the times tested, was significantly higher for the slices preserved in the solution of this invention (NPS) than with any of the other solutions tested ($p<0.0001$) for up to 24 hours. For all solutions, the greatest decline in ATP levels occurred during the first six hours of storage. For the solution of the invention, decline in ATP levels was approximately 50% over this time interval, compared with a 60% decline for the Columbia solution and an 80% decline for the LTW solution.

For the solution of the invention, ATP levels at both the zero and 6-hour time points were higher than levels seen at the zero hour time points for any of the other preservation solutions, indicating significantly better levels of ATP preservation. ATP levels in the slices stored in the solution continued to decline an additional 33% from 6 to 24 hours, indicating a slow decline in ATP levels over the subsequent 18 hours. At the 24 hour time point, remaining ATP levels with storage in the solution of the invention approximated those seen at the zero hour time point for the other solutions, indicating durable preservation of ATP energy stores.

EXAMPLE 2

Rat heart slices were obtained and preserved as above in Example 1. At time 0, six, twelve, eighteen, and 24 hours after slicing, six slices were removed from each of the preservative solutions and tested for protein synthesis.

Protein synthesis was measured by incorporation of radiolabeled leucine into acid precipitable proteins. Following cold storage, the slices were placed onto Teflon/titanium rollers, loaded into glass scintillation vials and incubated at 37° C. in Waymouth's solution (Gibco, Grand Island, N.Y.) containing [$^3$H] Leucine (New England Nuclear, Boston, Mass.) at 0.3 mCi/ml (prepared with 60 ml [$^3$H] Leucine in 200 mls of Waymouth's solution for four hours in the Vitron dynamic organ incubator (Vitron, Tucson, Ariz.). The incubated slices were weighed, washed twice in buffer and homogenized in 1 ml of 1N KOH. Twenty ml aliquots of the homogenates were then pipetted off and 1 ml of 1.5N acetic acid added. The solution was then left to stand for 24 hours at 4° C. The solution was then spun at 3,250 rpm for 15 minutes. The resulting pellet was washed two more times in 1 ml volumes of 1N HCl and then dissolved in 0.5 ml of 0.5N NaOH. The incorporation of [$^3$H] Leucine into acid precipitable protein was determined by counting a 0.5 ml aliquot of the dissolved pellets after neutralization with 125 ml of 2N HCl.

Figure 2:
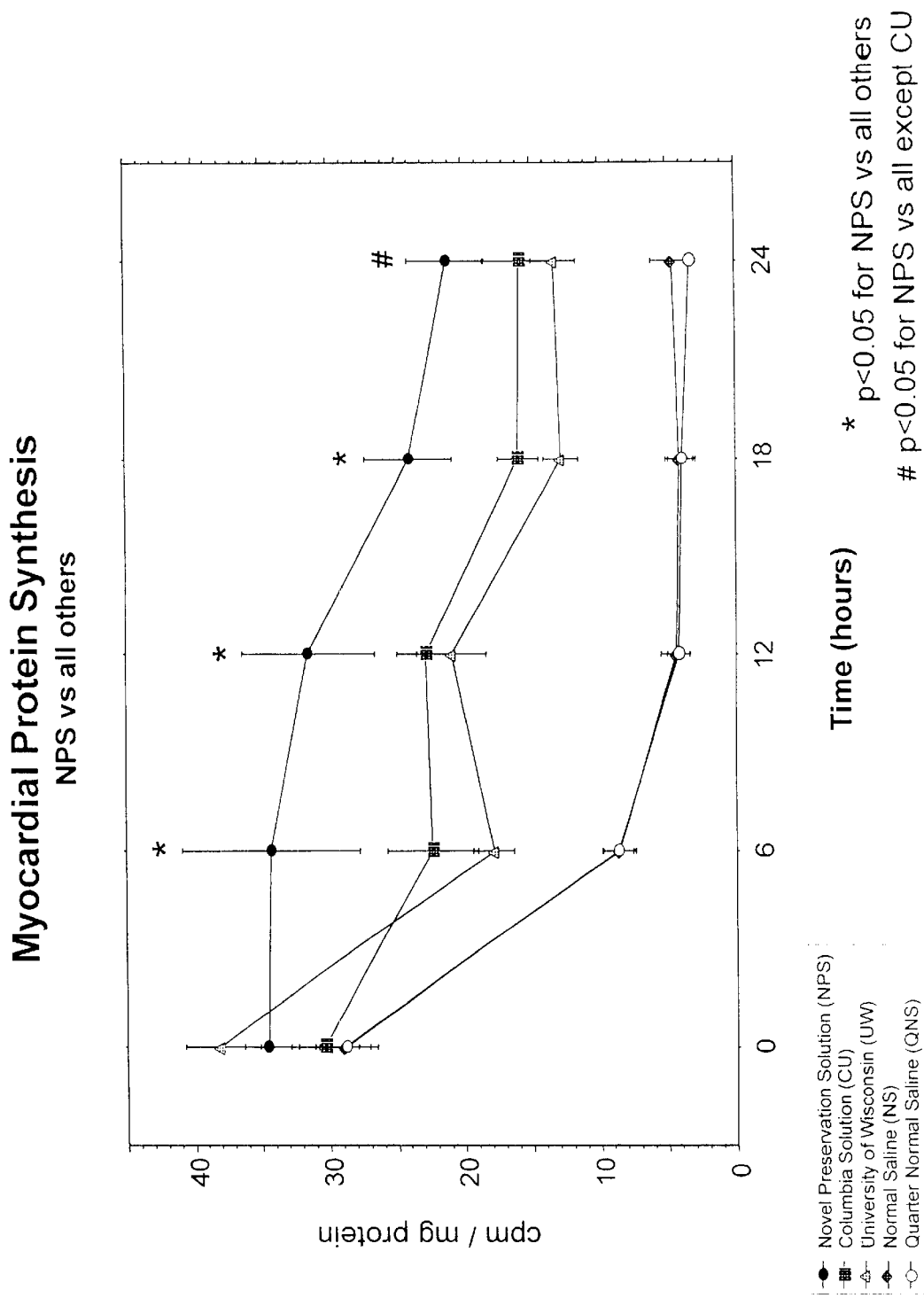
FIG. 2 is graph of the protein synthesis of myocardial tissue, bathed in 4 different preservation solutions, as described in the example, infra.

Results are expressed as counts per minute (cpm) of $^3$[H] leucine incorporated per mg of protein. (FIG. 2). The data was analyzed using analysis of variance and are presented as the mean + standard deviation. As shown in FIG. 2, capacity for protein synthesis in the stored heart slices was significantly higher with storage in the solution of the invention compared to all other solutions for 6, 12 and 18 hours of storage ($p<0.05$). As expected, there was no significant difference between the solutions at the zero time point. Storage in the solution of the invention showed maintenance of capacity for protein synthesis, without significant degradation, until beyond the 18 hour time point. At 24 hours, the capacity for protein synthesis remained significantly higher for storage in the solution of the invention compared to all other solutions with the exception of the Columbia solution, where the increase was not statistically significant. Among the other solutions, there was an immediate decline in protein synthesis to the 6-hour time point, which carried through to 24 hours of storage.

Removal of trehalose or arginine from the solution of the invention resulted in ATP levels and capacity for protein synthesis which approximated that seen with certain of the other solutions (e.g. Columbia solution). Additional removal of second messenger components from the solution of the invention including db-cAMP and nitroglycerin resulted in a further decline in preservation of myocardial biochemical function to levels approximating the UW solution. db-cAMP is a membrane permeable cAMP analogue (Oz et al., *Circulation* 88:II-291 (1993)). With hypoxia there is a fall in intracellular c-AMP levels due to reduced adenylate cyclase activity. Restoration of c-AMP during ischemia restores endothelial barrier function, modulates leukocyte and endothelial cell interactions and improves intracellular c-AMP levels. (Oz et al., *Circulation* 88:II-291 (1993)).

Thus, both ATP levels and capacity for protein synthesis were significantly higher for tissue in the solution of the invention compared to all others at all time points. This indicates improved preservation of energy stores and maintenance of cellular integrity. While not wishing to be bound by any particular theory, the superior performance of the solutions of the invention may be due to the presence of trehalose and/or L-arginine. Removal of trehalose and arginine from the solution resulted in ATP levels and capacity for protein synthesis which closely approximated that seen with the Columbia solution, indicating that these three components may be significant. Trehalose is a disaccharide consisting of two glucose moieties, which can be hydrolyzed to glucose by trehalase. In addition to acting as a possible energy source, trehalose stabilizes and protects cell membranes under stress including desiccation, freezing and elevated temperatures (Wada et al., *Ann. Thorac. Surg.* 61:963 (1996)). L-arginine appears to improve organ preservation by augmentation of the nitric oxide pathway, which helps to maintain vascular homeostasis, inhibit leukocyte adhesion and inhibit platelet aggregation. Larginine also improves the recovery of endothelial function during reperfusion after myocardial ischemia (Shiraishi et al., *Ann. Thorac. Surg.* 62:1580 (1996)). Glutathione acts to reduce the level of oxidants generated at the time of reperfusion (Jeevanandam et al., *J. Thor. Cardiovasc. Surg.* 104:224 (1992)). Similarly, allopurinol acts to suppress the generation of oxygen free radicals by inhibition of the activity of xanthine oxidase.

The other components of the solutions of the invention are also believed to convey important properties to the solution. For example, adenosine serves to preserve and restore the regeneration of ATP during reperfusion. Magnesium acts as a membrane stabilizing agent (Jeevanandam et al., *supra*). Nitroglycerin leads to an increase in nitric oxide levels, helping to minimize the deleterious cell-cell interactions which occur during cold storage and reperfusion (Oz et al., *supra*). Dextran, acts as a membrane stabilizing agent and reduces the cell edema associated with hypothermic storage by decreasing transcapillary and osmotic fluid flow (Oz et al., *supra*, and Jeevanandam et al., *supra*). The intracellular composition of electrolytes in the solution of the invention decreases the gradient for sodium and potassium transport across the cell membrane preventing sodium influx into the cells, thereby reducing obligatory transport of water, and, consequently, cell edema (Jeevanandam et al., *supra*). The reduction in sodium and potassium transport across the cell membrane serves to preserve ATP levels that otherwise would be consumed in the sodium-potassium ATP pump.

Thus, the components of the solutions of the invention preserve the structure and function of cell membranes and supplement second messenger pathways, particularly nitric oxide. Maintenance of the structure and function of cell membranes is critical for cells to maintain viability during the rigors of cold storage, while optimization of nitric oxide levels minimizes deleterious cell-cell interactions during cold storage and reperfusion.

The tissue slice method described in this Example provides a rapid procedure for assessing the performance of organ preservation solutions, such as the myocardial preservation solution of the invention, permitting the effect of individual solution components and other variables to be tested using quantifiable biochemical endpoints.

EXAMPLE 3

The performance of the novel preservation solutions of the invention on intact organs such as the heart are evaluated as follows. A perfusion circuit is established in which the functions of the heart and lung of the animal subject are managed by the circuit during the experimental procedures. Adult rabbits are used to provide a "donor" animal which supplies the heart and a "support animal" to support the heart on the circuit. All surgeries are performed aseptically using appropriate anesthesia. The anesthetic is selected to minimize cardiovascular side effects or myocardial depression, and thus is preferably not an inhalation anesthetic. The narcotic fentanyl is used in combination with droperidol and infused continually. Initial sedation and anesthesia are obtained using an intramuscular injection of 0.05 mg/kg fentanyl and 2.5 mg/kg droperidol.

The support animal is placed in the supine position, shaved, sterilely prepped, and a tracheostomy is performed. Mechanical ventilation is started using 100% oxygen, further anesthetic (0.04 mg/kg fentanyl intravenously (IV)) and heparin (1000 units IV) are administered.

In the donor animal, a median sternotomy is performed, and the heart is arrested using an IV bolus of potassium chloride (4 mEq), excised, flushed and cold-stored for 2, 4, 8, 12 and 24 hours in the heart preservation solution of the invention.

The support animal, after induction of anesthesia and tracheostomy, is attached in-line to the circulating perfusion circuit via cannullae (tubes) placed in both the carotid artery and jugular vein. Arterial pressure of the support animal is monitored for signs of hypovolemia or inadequate anesthesia via a line placed in the femoral artery. Additional heparin (300 units IV) is administered hourly. Temperature is monitored using a rectal probe. The circuit oxygenation, acid-base balance, hematocrit and electrolyte balance are monitored every 15 to 30 minutes by arterial sampling. Blood procured from the support animal is used to transfuse the donated heart and to prime the circuit.

The donated heart is stabilized on the circuit for 30 minutes, and its function is assessed in a working mode for 3.5 hours perfusing the left atrium and measuring cardiac output, developed pressure, stroke work and coronary flow. Venous effluent from the reperfused heart is sampled for oxygen extraction, lactate levels, Creatine Phosphokinase (CPK) release (an indicator of heart muscle damage) and myeloperoxidase activity as a measure of reperfusion injury. At the conclusion of reperfusion, the myocardium is sampled for sodium, potassium and calcium content using flame photometery, adenine nucleotide content is determined using HPLC. In addition, glycogen content, and metabolic intermediate content such as pyruvate, lactate, aspartate and a-ketoglutarate levels are determined. Light microscopy is also performed for histologic examination. "Control" values are established using a group of rabbit hearts procured and immediately reperfused without storage. Following the evaluation period, the support animal is euthanized using a lethal dose (4 mEq IV) of potassium chloride.

The data obtained in this experiment provides additional data with the tissue slice biochemical data of the physiological health of the organ after storage in the preservation solutions of the invention.

EXAMPLE 4

Rat lungs were dissected out from adult Sprague-Dawley rats. Agarose gel at 37° C. is then instilled via the trachea to solidify the lung parenchyma. The solidified lung tissue is then precision cut using a mechanical tissue slicer (Vitron, Tucson, Ariz.) into 200 μm diameter slices as described above for heart tissue in Example 1. The slices were preserved at 4° C. in: 1) solution 1 ("Low Potassium-Dextran Solution")(refer to Table 5)(Keshavjee et al., *J. Thorac. Cardiovascular Surg.* 98:529–534 (1989)); 2) normal saline ("NS"); 3) UW (refer to Table 2); 4) Euro-Collins solution ("EC") (refer to Table 6) (Collins et al., *Lancet* 2:1219 (1969)); 5) Kyoto solution (refer to Table 7) (Wada et al., *Ann. Thorac. Surg.* 61:963–968 (1996)); or 6) the solution of this invention (m-US+c-GMP, refer to Table 4).

The following ingredients and amounts were used to prepare the lung solution of the invention:

TABLE 4 m-US + c-GMP Solution

| | | |
|---|---|---|
| 2.72 | g/L | potassium phosphate (20 mmol/L) |
| 1.93 | g/L | magnesium sulfate (15 mmol/L) |
| 0.11 | g/L | calcium chloride (1 mmol/L) |
| 30.0 | g/L | trehalose |
| 10,000 | units/L | heparin |
| 30.0 | g/L | dextran |
| 100 | mg/L | nitroglycerin |
| 1.34 | g/L | adenosine (5 mmol/L) |
| 0.14 | g/L | allopurinol (1 mmol/L) |
| 0.92 | g/L | glutathione (reduced, 3 mmol/L) |
| 89.2 | mg/L | 8-Bromo-c-GMP (200 mmol/L) and |
| 16.0 | mg/L | Dexamethasone |

The ingredients were added at room temperature using constant stirring. After adding the allopurinol, the solution was brought up to a volume of 980 ml using distilled water. 0.92 g/l of glutathione (reduced, from 3 mmol/l) was dissolved in 20 ml of distilled water and the pH adjusted to approximately 7.4 using potassium hydroxide (KOH). KOH was also used to bring the main solution up to a pH of 7.4. After both solutions were at a pH of 7.4 the glutathione solution was added to the main solution. Then, 89.2 g/l of 8-Bromo-c-GMP (200 mmol/L) and 16.0 mg/L of dexamethasone were added and the final pH was adjusted to 7.4.

TABLE 5

Low Potassium-Dextran Solution

| | |
|---|---|
| 168 mmol/L | sodium |
| 4 mmol/L | potassium |
| 103 mmol/L | chloride |
| 37 mmol/L | phosphate |
| 2 mmol/L | magnesium and |
| 020 g/L | dextran 40 |

TABLE 6

Euro-Collins Solution

| | |
|---|---|
| 2.05 g/L | potassium dihydrogen phosphate |
| 7.4 g/L | potassium monohydrogen phosphate |
| 1.12 g/L | potassium chloride |
| 0.84 g/L | sodium bicarbonate |
| 1.00 g/L | magnesium sulfate |
| 6.50 g/L | glucose monohydrate |

TABLE 7

Kyoto Solution

| | |
|---|---|
| 100 mmol/L | sodium |
| 44 mmol/L | potassium |
| 100 mmol/L | gluconate |
| 25 mmol/L | phosphate |
| 4.1% | trehalose and |
| 3% | hydroxyethyl starch (pentafraction) |

Figure 3:
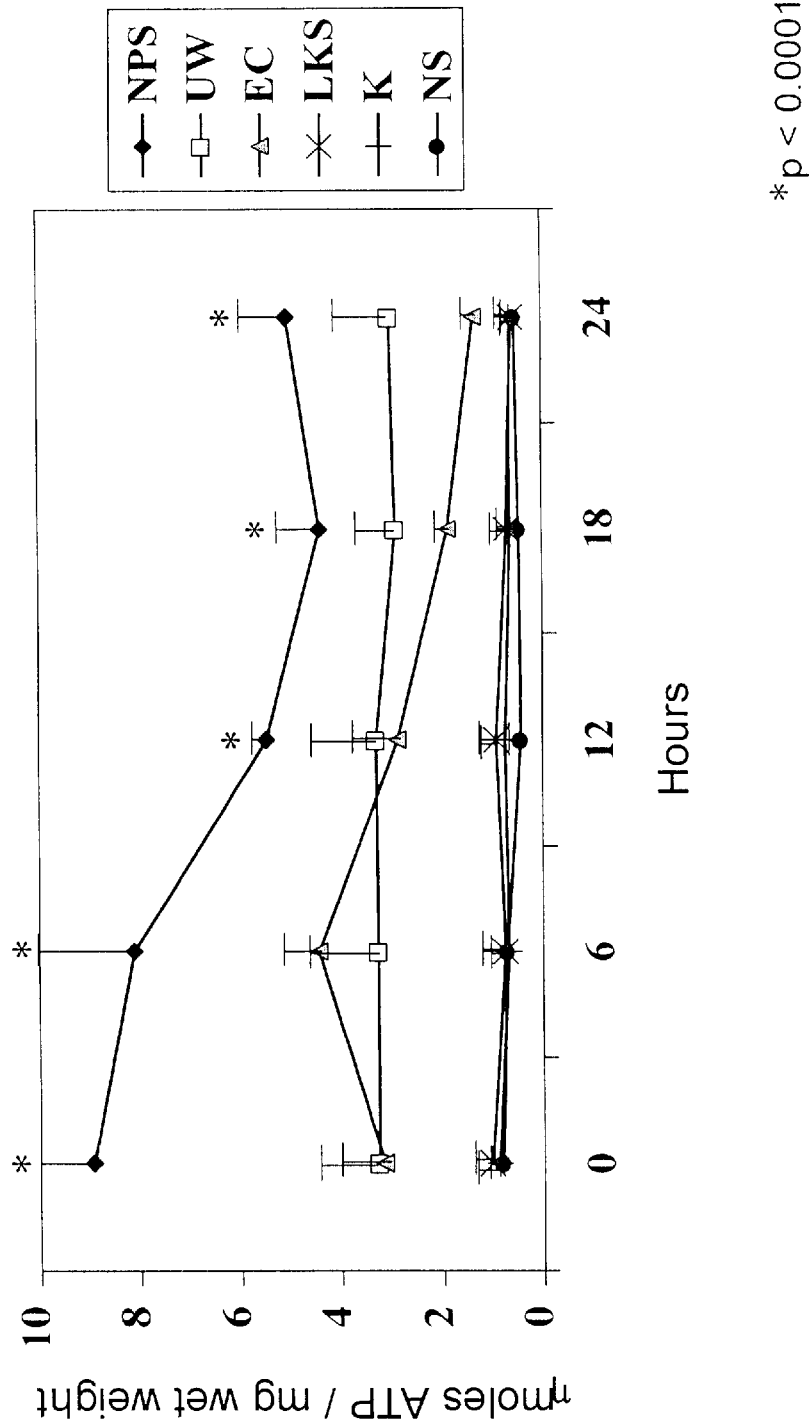
FIG. 3 is a graph of the ATP content of lung tissue, bathed in 6 different preservation solutions, as described in the example, infra.
Figure 4:
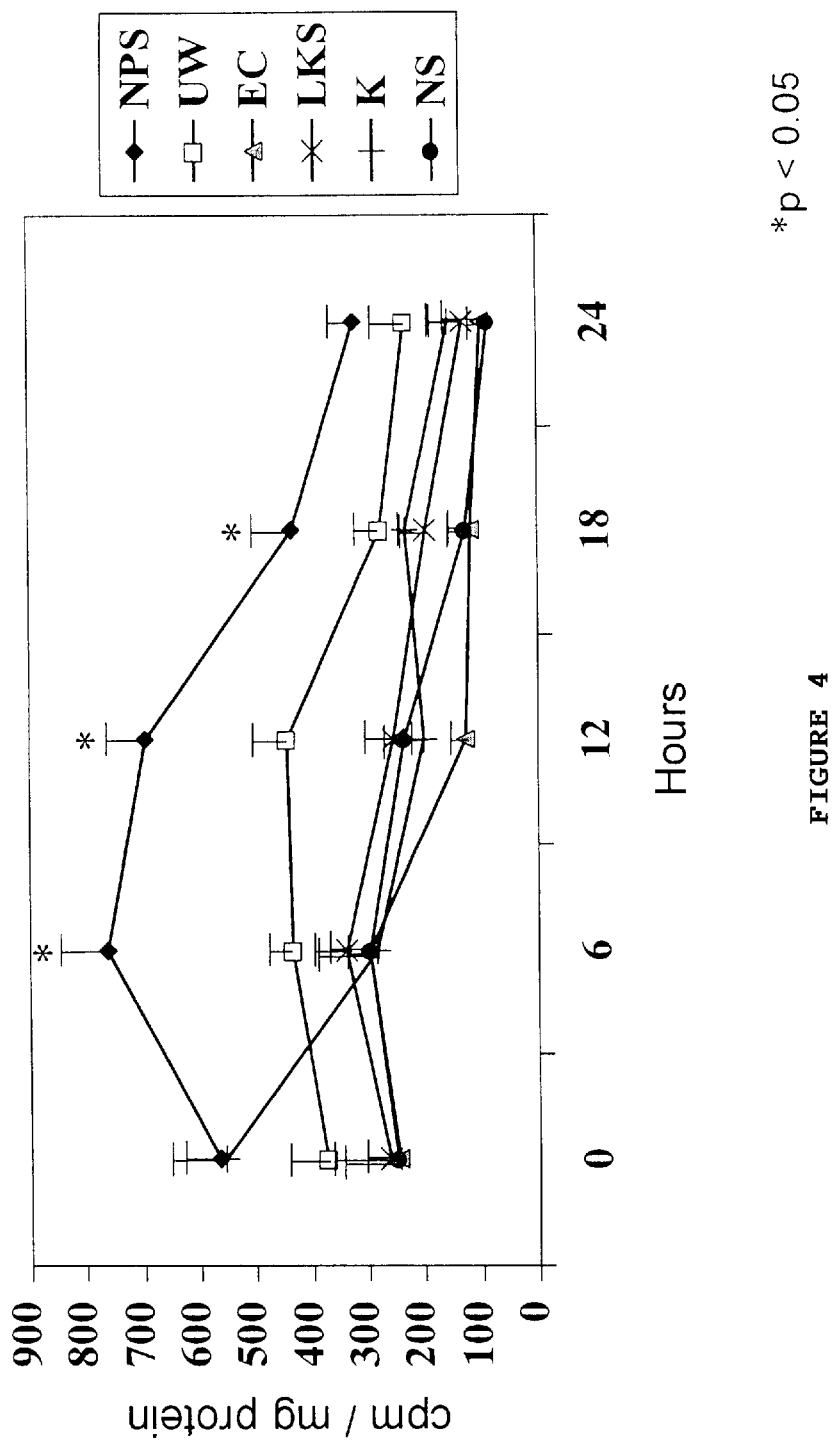
FIG. 4 is a graph of the protein synthesis of lung tissue, bathed in 5 different preservation solutions, as described in the example, infra.

Lung cellular viability was assessed in the following manner. Immediately following slicing (time 0) six slices from each of the six (6) solutions were assayed using the luciferin-luciferase bioluminescent assay to determine the ATP content of the slices. The assay was repeated for six new slices at each of 6, 12, 18, and 24 hours after slicing. The results were expressed as nanomoles of AT?/mg of wet weight of lung tissue (FIG. 3). The data were analyzed using analysis of variance and are presented as the mean ± standard deviation.

Protein synthesis was also determined as described above in Example 2.

Results

As shown in FIG. 3, the ATP content for the slices, at each of the times tested, was significantly higher for the slices preserved in the solution of this invention than with any of the other solutions tested ($p<0.0001$) for up to 24 hours.

The capacity for protein synthesis with storage of lung tissue in the solution of the invention (m-US +c-GMP Solution) was significantly higher than for all other test solutions at 6, 12 and 18 hours ($p<0.05$).

The above results demonstrate that the organ preservation solutions of the invention provide improved viability of organ tissue in vitro as determined by increased ATP production and protein synthesis.

Various publications cited herein are hereby incorporated by reference in their entirety herein.

As will be apparent to those skilled in the art to which the invention is addressed, the present invention may be embodied in forms other than those specifically disclosed above without departing from the spirit or potential characteristics of the invention. Particular embodiments of the present invention described above are, therefore, to be considered in all respects as illustrative and not restrictive. The scope of the present invention is as set forth in the appended claims and equivalents thereof, rather than being limited to the examples contained in the foregoing description.

We claim:

1. A solution for preserving and/or maintaining the viability of an organ or tissue of that organ, comprising a sufficient amount of trehalose, anti-oxidant, cations, wherein said cations include calcium, and an energy source effective to support intracellular function and maintain cellular viability.

2. The solution of claim 1 wherein said energy source is cyclic AMP, cyclic GMP or adenosine.

3. The solution of claim 1 wherein said anti-oxidant is glutathione and/or allopurinol.

4. The solution of claim 1 further comprising an anticoagulant, a polysaccharide distinct from said cryopreservative agent nitroglycerin, and at least one amino acid.

5. The solution of claim 4 wherein said cations further comprise potassium, and magnesium.

6. The solution of claim 4 comprising:
   from 0.01 g/L to 10 g/L of cations;
   from 3 g/L to 100 g/L of trehalose;
   from 100 to 30,000 units/L of an anticoagulant;
   from 25 g/L to 40 g/L of a polysaccharide distinct from trehalose;
   from 0.10 g/L to 10 g/L of an amino acid;
   from 0.01 g/L to 10 g/L of an anti-oxidant; and
   from 0.01 g/L to 10 g/L of an energy source.

7. The solution of claim 6 wherein the pH is approximately 7.4.

8. The solution of claim 6 comprising:
   2.72 g/L potassium phosphate;
   1.93 g/L magnesium sulfate;
   0.11 g/L calcium chloride;
   30.0 g/L trehalose
   10,000 units/L heparin
   30.0 g/L dextran
   100 mg/L nitroglycerin
   1.34 g/L adenosine;
   1.74 g/L L-arginine;
   0.14 g/L allopurinol;
   0.92 g/L reduced glutathione; and
   0.98 g/L db-cyclic AMP; at a pH of 7.4.

9. The solution of claim 1 wherein the pH is from 7.0 to 8.0.

10. The solution of claim 1 wherein said organ or tissue is heart or lung.

11. A method of preserving and/or maintaining an organ or portion thereof comprising contacting said organ or portion thereof with the solution of claim 1.

12. The method of claim 11 wherein the organ or portion thereof is heart.

13. A method of transplantation of an organ or portion thereof comprising grafting an organ or portion thereof and perfusing with the solution of claim 1.

14. The method of claim 13 wherein said organ or portion thereof is a heart or lung.

15. A solution for preservation and protection of an organ or tissue of that organ, comprising
   from 0.03 g/L to 10 g/L cations, wherein said cations include calcium;
   from 3 g/L to 100 g/L of a cryopreservative agent comprising a chain of at least two simple sugars;
   from 100 units/L to 30,000 units/L of an anticoagulant;
   from 25 g/L to 40 g/L of polysaccharide distinct from said cryopreservative agent;
   from 10 mg/L to 1000 mg/L of nitroglycerin;
   from 0.10 g/L to 10 g/L of an amino acid:
   from 0.01 g/L to 10 g/L of an anti-oxidant; and
   from 0.01 g/L to 10 g/L of an energy source.

16. The solution of claim 15 wherein said cryopreservative agent is trehalose, said anticoagulant is heparin, said polysaccharide is dextran, said amino acid is arginine, said anti-oxidant is glutathione and/or allopurinol and said energy source is cyclic GMP, cyclic AMP or adenosine.

17. The solution of claim 16 wherein said cations further include magnesium, and potassium.

18. The solution of claim 15 wherein said energy source is 8-bromo-cyclic GMP.

19. The solution of claim 15 wherein said organ or tissue is lung.

20. The solution of claim 15 wherein the pH is from 7.0 to 8.0.

21. The solution of claim 15 comprising:
   2.72 g/L potassium phosphate;
   1.93 g/L magnesium sulfate;
   0.11 g/L calcium chloride;
   30.0 g/L trehalose
   10,000 units/L heparin
   30.0 g/L dextran
   100 mg/L nitroglycerin
   1.34 g/L adenosine;
   0.14 g/L allopurinol;
   0.92 g/L reduced glutathione;
   89.2 mg/L 8-bromo-c-GMP; and
   16.0 mg/L Dexamethasone at a pH of 7.4.

22. The solution of claim 21 wherein said organ or tissue is lung.

23. A method of preserving and protecting an organ or portion thereof comprising contacting said organ or portion thereof with the solution of claim 15 or 21.

24. A method of transplantation of an organ or portion thereof comprising grafting an organ or portion thereof and perfusing with the solution of claim 15 or 21.

25. The method of claim 23 or 24 wherein the organ or portion thereof is lung.

* * * * *